US00PP27710P3

(12) United States Plant Patent
Byrne et al.

(10) Patent No.: US PP27,710 P3
(45) Date of Patent: Feb. 28, 2017

(54) PEACH TREE NAMED 'ROYAL ZEST THREE'

(50) Latin Name: *Prunus persica*
Varietal Denomination: Royal Zest Three

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 123 days.

(21) Appl. No.: 14/544,509

(22) Filed: Jan. 13, 2015

(65) Prior Publication Data

US 2016/0205837 P1 Jul. 14, 2016

(51) Int. Cl.
*A01H 5/08* (2006.01)

(52) U.S. Cl.
USPC ..... Plt./198

(58) Field of Classification Search
USPC ..... Plt./197, 198
See application file for complete search history.

(56) References Cited

U.S. PATENT DOCUMENTS

PP7,290 P 8/1990 Zaiger et al.

OTHER PUBLICATIONS

The Brooks and Olmo Register of Fruit and Nut Varieties, 3rd Ed., American Society of Horticultural Science Press, Alexandria, VA, 1997.

Brooks, R. M. 1958. Double Delight, Earligold, and June Gold peaches. Fruit Var. J. 3:22.

Okie, W. R. 1993. 'Goldprince' and 'Scarletpearl' peaches. HortScience 28:231.

Rouse, R. and W. Sherman. 1989. 'TropicBeauty': a low-chilling peach for subtropical climates. HortScience 24:165-166.

*Primary Examiner* — Anne Grunberg
(74) *Attorney, Agent, or Firm* — Ramey & Schwaller, LLP

(57) ABSTRACT

Disclosed is a new variety of *Prunus persica* named 'Royal Zest Three'. This new variety, which requires approximately 550 chilling units of dormancy, is considered to be a peach tree of mid-season maturity, which produces yellow fleshed freestone fruit that are very firm, attractively colored, and suitable for both local and regional markets.

4 Drawing Sheets

BACKGROUND OF THE INVENTION

Field of the Invention

This invention relates to peach trees and, more specifically, to peach trees referred to as a variety of *Prunus persica* named 'Royal Zest Three'. 'Royal Zest Three', which requires approximately 600 chilling units of dormancy, produces an exceptionally high quality, firm freestone peach that matures mid-season.

SUMMARY OF THE INVENTION

The 'Royal Zest Three' peach is characterized as to novelty and is otherwise noteworthy by producing fruit that ripens in the mid-season; is considered high quality; and which is firm and has an attractive coloration. In this regard, the present variety of peach tree bears fruit that are ripe for commercial harvesting and shipment in early to mid-June, when the fruit is grown in medium chill zone of Texas. 'Royal Zest Three' ripens about 10 days later than 'June Gold' Peach, a non-patented variety (Brooks, R. M. 1958. Fruit Var. J. 3:22). Additionally, the new variety exhibits the potential to be commercialized in regions that have chilling requirements that are relatively low.

ORIGIN OF THE VARIETY

The present peach tree was the result of an ongoing Stone Fruit Breeding Program of Texas A & M University, College Station, Brazos County, Tex. To this end, controlled crosses are made each year in order to produce seedling populations from which improved progenies are evaluated and selected.

The seedling TX4E218 ("Royal Zest Three") was discovered at the Texas A & M University Horticultural Farm in College Station, Tex. in 2002 in a population of seedlings that resulted from seed from a cross between the yellow-fleshed California peach 'Rich Lady' U.S. Plant Pat. No. 7,290 and the early ripening, medium chill peach, 'Victor' (UPOV PBR PRUNU_PER grant #25391). 'Victor' was released by Texas A&M University for use in Spain and is a seedling from the cross between the low chill, yellow-fleshed, mid-season cultivar 'Tropic Beauty' (not patented) and the early ripening, yellow-fleshed, medium chill peach 'Goldprince' (not patented). 'Tropic Beauty' was jointly released by the University of Florida and Texas A&M University (Rouse and Sherman, 1989) and is derived from a cross between an unreleased Florida selection Fla3-2 (K6E121 open pollinated) and 'Flordaprince' (Fla2-7× 'Maravilha') (not patented, Sherman and Lyrene, 1992). 'Goldprince' was released by the USDA breeding program in Byron, Ga. (Okie, 1993) and is derived from a cross between 'Loring' (not patented, Okie, 1998) and the unreleased Georgia selection FV3-257. Resulting seed from this cross were planted in 1999 at the Texas A & M University Horticultural Farm in College Station, Tex. 'ROYAL ZEST THREE' was marked as TX4E218 for subsequent observation and noted as having exceptional characteristics. Two-year and older trees of the variety were subsequently evaluated during the 2005 through 2013 fruit growing seasons in both California (Fowler) and Texas (Terrell, Fairfield and College Station).

The new variety 'Royal Zest Three' differs from 'Rich Lady', its yellow-fleshed, high chill female parent as it requires less chilling (approx. 600 chill hours versus approx. 800), blooms 5-9 days earlier, ripens 2-3 days earlier, and has a more rounded shape.

'Royal Zest Three' differs from, 'Victor', its medium chill, yellow fleshed peach as it requires more chilling accumulation to break dormancy (600 versus 400 chilling hours), blooms 10-11 days later, ripens 3-4 weeks later, and has more red blush development (~65% versus 55%).

Asexual Reproduction of the Variety

'ROYAL ZEST THREE' was bud grafted onto virus-free Nemaguard ("The Brooks and Olmo Register of Fruit and Nut Varieties," 3rd Ed., American Society of Horticultural Science Press, Alexandria, Va., 1997, unpatented) peach rootstock in June 1998 at the nursery site in Oakdale, Calif. The variety was subsequently planted at the experimental orchard in the central portion of the San Joaquin Valley, near Fowler, Fresno County, Calif. and in three sites in Texas (College Station, Fairfield, and Terrell). Fruit from the resulting propagation has been evaluated during the period from 2000 to 2008 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographic drawings and depicts the plant by the best possible color representation using color photography, wherein.

BOTANICAL DESCRIPTION OF THE VARIETY

Figure 1:
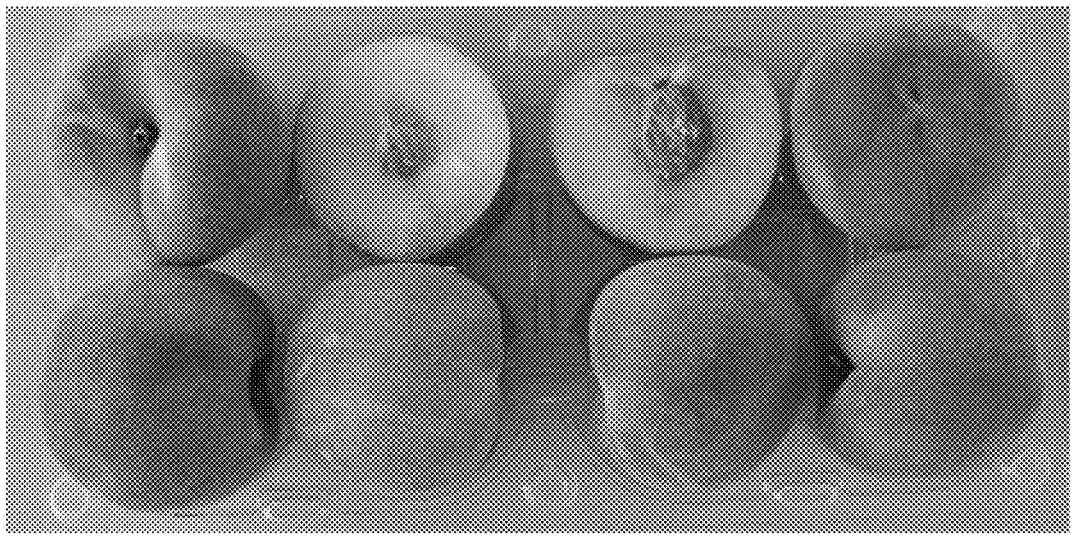
FIG. 1. Color picture showing the flesh and skin color and fruit shape of 'Royal Zest Three'.
Figure 2:
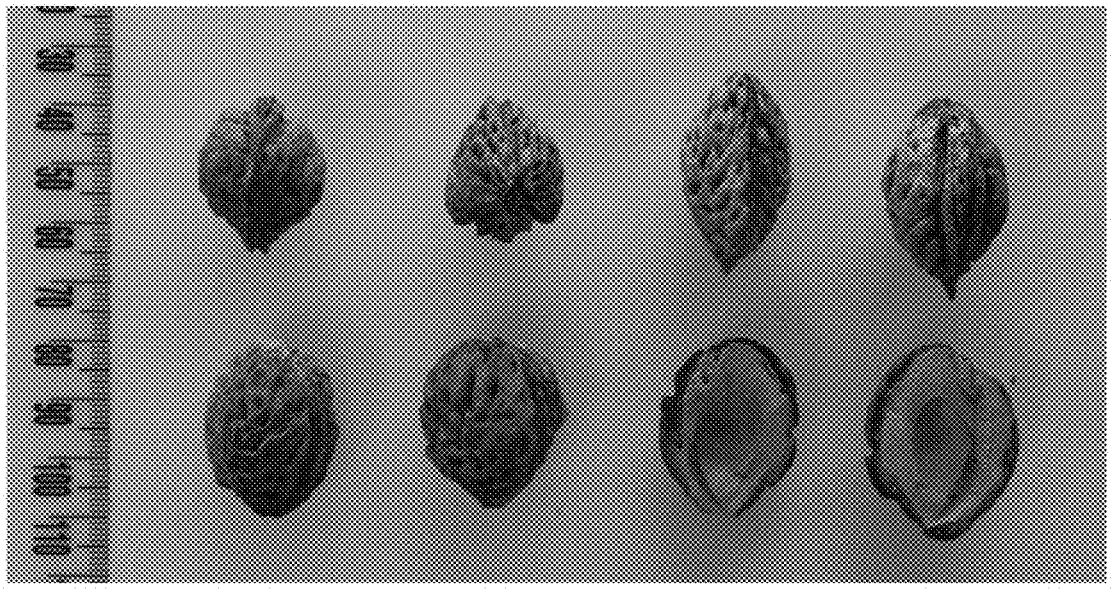
FIG. 2. The endocarp of 'Royal Zest Three'. The ruler is in millimeters.
Figure 3:
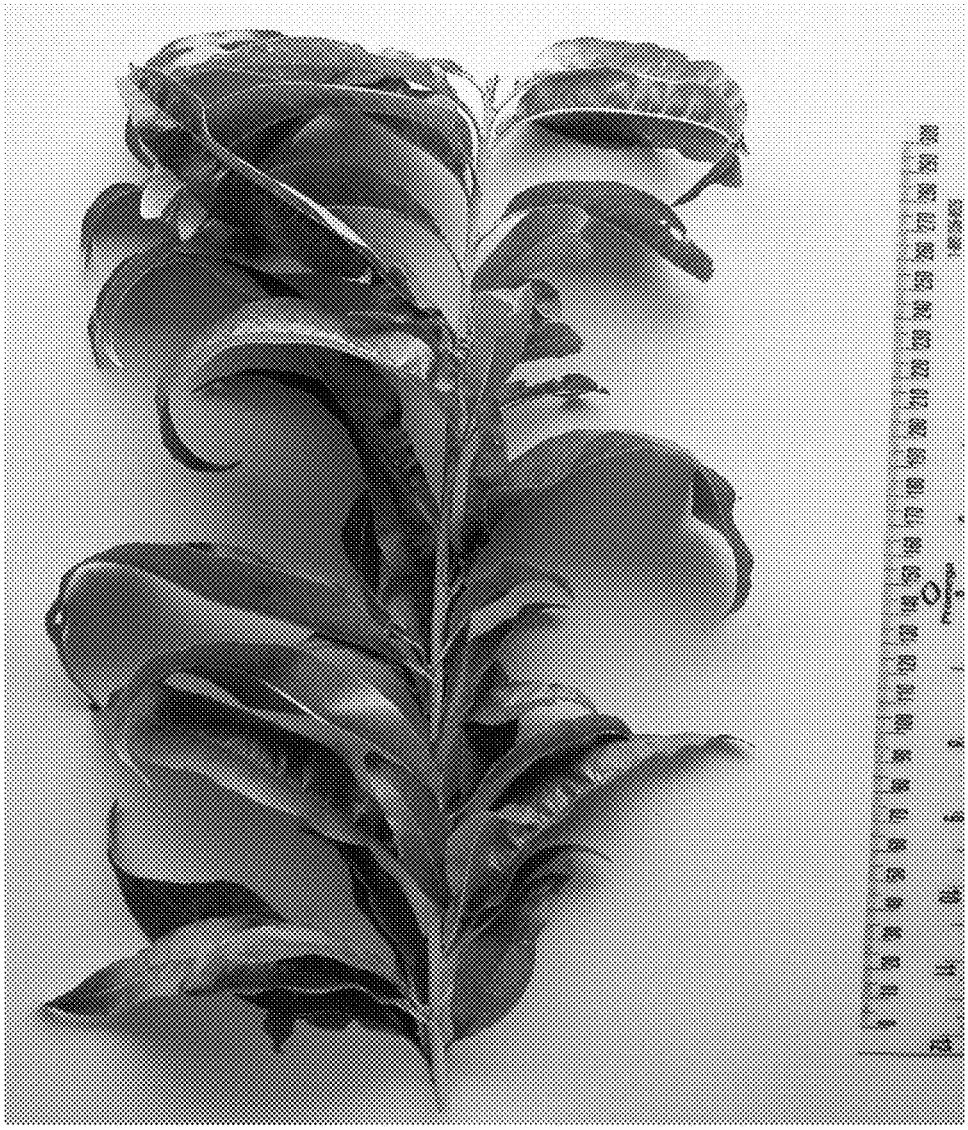
FIG. 3. A stem showing the leaves of the 'Royal Zest Three' peach. The ruler is demarcated in millimeters.
Figure 4:
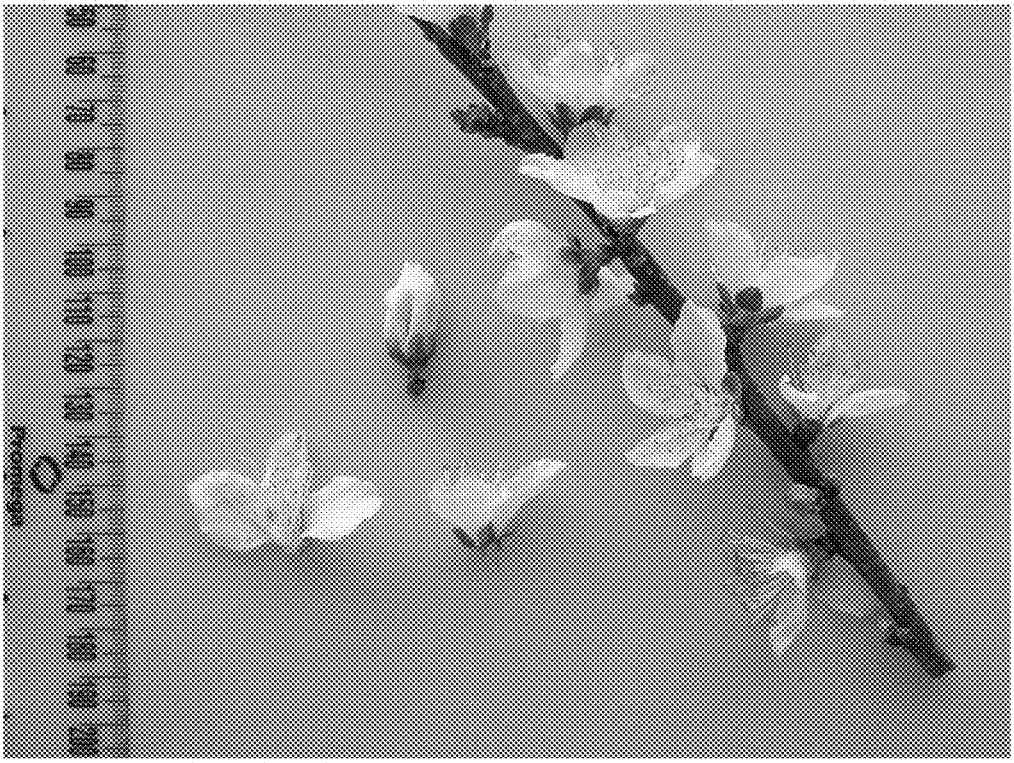
FIG. 4. The showy flowers of 'Royal Zest Three'. The ruler is in millimeters.

Referring more specifically to the pomological details of this new and distinct variety of peach tree, the following has been observed under the ecological conditions prevailing at the experimental orchards in medium chill zone of Texas. All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars ripening in the mid-season of maturity.

*Height*.—7 feet (2.13 m) at the end of the 2012 growing season.

*Width*.—6 feet (1.83 m) at the end of the 2012 growing season.

*Vigor*.—High.

*Density*.—Medium to high.

*Productivity*.—Productive.

*Shape*.—The trees are vigorous with the typical semi-spreading growth habit similar to 'TexKing' (U.S. Plant Pat. No. 14,627), 'TexPrince' (U.S. Plant Pat. No. 14,629), and 'TexRoyal' (not patented, Byrne and Bacon, 1991).

*Current season growth*.—The current season growth for the new variety was approximately 2.9 to 3.8 feet (0.88-1.2 m).

*Regularity of bearing*.—Regular, and considered hardy under typical conditions found in the medium chill zone of Texas and the central San Joaquin Valley, Calif.

Trunk:

*Size*.—Approximately 3.5 inches (8.89 cm) in diameter and 14 inches (35.56 cm) in circumference when measured at a distance of approximately 12 inches (30.5 cm) above the soil level, at the end of the 2012 growing season on a five-year old tree.

*Bark texture*.—Considered moderately rough with numerous folds of papery scarf-like skin being present.

*Bark coloration*.—Variable, colors present are 166A of the Greyed-Orange Group and 200C-D and N200C of the Brown Group.

Branches:

*Size*.—Considered medium for the variety.

*Thickness*.—Average (about 6.4 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 5 to 10 mm in width and were approximately 1-2 mm in height.

*Current season shoots*.—Surface texture — Substantially glabrous.

*Internode length*.—Approximately 2.5 to 4.5 cm as measured in the middle of a current season stem.

*Color of mature branches*.—The predominant colors are 183A-B of the Greyed-Purple Group and 201A-C of the Grey Group.

*Current season shoots*.—Color — Light green (N144D and 144A-B of the Yellow-Green Group). The color of new shoot tips is considered a bright and shiny green (mainly Yellow-Green Groups N144D, 145A-B and 146D).

*Type of bearing*.—Long shoots only.

*Spur length*.—Not applicable.

*Vegetative bud size*.—Generally 2-4 mm in length on the mid portion of a late summer shoot.

*Vegetative bud shape of apex*.—Acute.

*Position of vegetative bud in relation to one-year-old shoot*.—Slightly held out.

Leaves:

*Size*.—Considered moderately large for the species. Leaf measurements have been taken from vigorous upright current season growth approximately at mid-shoot.

*Leaf length*.—Approximately 170 to 180 mm.

*Leaf width*.—Approximately 33 to 39 mm.

*Leaf thickness*.—Less than 1 mm.

*Leaf form*.—Lanceolate.

*Leaf tip form*.—Acuminate.

*Leaf upper surface color*.—Green varying among 137A-B of the Green Group.

*Leaf lower surface color*.—Green varying approximately 147D of the Yellow-Green Group.

*Leaf mid-vein color*.—Light yellow green (147A-D of the Yellow-Green Group).

*Leaf margins*.—Form — Considered crenate. Uniformity — Considered generally uniform.

*Leaf petioles*.—Size — Considered medium. Length — Approximately 10 to 12 mm. Thickness — Approximately 1 to 2 mm. Color — Pale green (Yellow-Green Group 144A-C).

*Leaf glands* (*nectaries*).—Size — Approximately 1 mm or less in height and width. Number — Generally 0-3 per leaf. Type — Globose. Color — Brown (N200A Brown Group). Position — predominantly on the base of the leaf blade.

*Leaf stipules*.—Size — Medium for the species. Length — Approximately 9 to 11 mm. Form — Lanceolate. Color — Green (144B-C of the Yellow-Green Group) with reddish brown tips when young. The stipules are early deciduous.

*Ratio of wood* (*leaf*) *buds to flowering buds*.—1 to 2 flower buds per vegetative bud.

Flowers:

*Floral buds*.—General — The floral buds are considered to be medium in size, conic in form, and slightly appressed relative to the bearing shoot. Color — The bud scales are silver-brown, (approximately Greyed-Green Group 197A-B, Grey-Brown Group N199B and the Brown Group 200B-C). The buds are considered hardy under the typical climatic conditions of the medium chill zone of Texas and the central San Joaquin Valley, Calif. Length — Approximately 5 to 6 mm. Blooming Type — Considered early in relation to other peach cultivars commonly growing in the medium chill zone of Texas. Date of full bloom was between February 28th and March 10th during the period between 2006 and 2011. The mean flowering time was about the 5th of March, 4-6 days before flowering of 'June Gold'.

*Flower fertility*.—Self fertile.

*Flower type*.—Showy.

*Flower size*.—Flower diameter at full bloom is approximately 33 to 41 mm.

*Bloom quantity*.—Considered abundant.

*Flower bud frequency*.—Normally 1 to 2 per node.

*Petal size*.—General — Considered medium large to large for the species. Width — Approximately 11 to 14 mm. Length — Approximately 20 to 22 mm.

*Petal form*.—Broadly ovate.

*Petal count*.—Nearly always 5.

*Petal color*.—Light pink when young (Red-Purple Group 62D, 69A-D and 73D), becoming darker near the petal claw (Red-Purple Group 62B-C, 63D and 65A-B).

*Flower arrangement of petals*.—Touching and/or overlapping at the base of the petals.

*Petal claw*.—Form — The claw is considered truncate in shape and has a medium size when compared to other varieties. Length — Approximately 1 to 2 mm. Width — Approximately 1 mm.

*Petal margins*.—Generally considered variable, from nearly smooth to slightly undulate.

*Petal apex*.—Generally — The petal apices appear slightly domed.

*Flower pedicel*.—Length — Considered long for the species, and having an average length of approximately 3 to 4 mm. Thickness — Considered average, approximately 1 mm. Color — A light green (Yellow-Green Group 144D, N144D and 145A-B).

*Floral nectaries*.—Color — Medium orange (Yellow-Orange Group 23A-B, Orange Group 24B, 25B-C, N25C and 26A). Calyx —.

*Surface texture*.—Generally glabrous. Color — Maroon with green (approximately Greyed-Red Group 178A-B, 181A, Greyed-Purple Group 183A-C, 185A and 187C). Sepals — Surface Texture — The surface has a very short, fine, wooly and a gray-colored texture. Size — Average, and ovate in form. Color — Maroon with green (approximately Greyed-Red Group 178A-B, 181A, Greyed-Purple Group 183A-C, 185A and 187C).

*Anthers*.—General — Average in size for the species. Color — Golden yellow (approximately Yellow Orange Group 17A-B and Greyed-Orange 163A-B). Pollen Production — Pollen is abundant and is a yellow color.

*Filaments*.—Size — Variable in length, approximately 16 to 18 mm, with the filaments slightly longer than the pistil. Color — Very light pink (approximately Red-Purple Group 62D and 65C-D) and darkening with advanced maturity. Anther position relative to pistil and petals — Anthers general at same height or higher than the pistils. The anthers do not protrude when the flower is at the pink bud stage of development.

*Pistil*.—General — Average in size, but slightly shorter, relative to the general anther height, overall. Length — Approximately 15 to 17 mm, including the ovary. Color — Considered a very light yellow-green when young (approximately Green-Yellow Group 1D and Yellow Group 2C-D and 4D). Surface Texture — The variety has a long, silver white pubescent pistil (approximately White Group 155A-D).

Fruit:

*Maturity*.—The present variety of fruit is described, as it would be found in its firm ripe condition at full commercial maturity. Under the ecological conditions prevailing in the medium chill zone of Texas. Over the period between 2006 and 2011 it ripen between June 6th and June 29nd with a mean first ripe date of June 13th in the medium chill zone of Texas.

*Size*.—General — Medium large to large for the season and considered uniform.

*Average cheek diameter*.—Approximately 62 to 68 mm.

*Average suture diameter*.—Approximately 61 to 69 mm.

*Average axial diameter*.—Approximately 63 to 70 mm.

*Fruit form*.—Generally considered truncate with unequal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. The suture is even or within 2-3 mm of being even with the surrounding fruit surface.

*Color*.—Orange-Red Group N34A, Red Group 42A and Red Group 53A-B.

*Ventral surface*.—Form — Considered uniform.

*Stem cavity*.—Size — Considered moderately large for the species. Width — Approximately 14 to 17 mm. Length — Approximately 23 to 35 mm. Depth — Approximately 12 to 18 mm.

*Fruit base*.—Round and flat.

*Fruit apex*.—Flat and round.

*Fruit stem*.—Length — 5 to 16 mm. Thickness — Approximately 3 to 5 mm. Color — Medium green with yellow green coloration (Green Group 143C and Yellow-Green Group 144A-C).

*Fruit skin*.—Generally considered medium or average in thickness. Surface Texture — Light, short pubescence. Skin Acidity — Considered neutral. Tenacious to Flesh — Yes. Tendency to Crack — Not observed. Skin Color — Generally — Variable, with approximately 65-85% of the fruit surface covered with an attractive red blush. Down — Light and short. Blush Color — The blush color is more apparent on the apical surface. It ranges from a dark red to a medium red (Red Groups 45A-B, 46A, 47A and 53A-B) with many degrees of shading and blending between the stated colorations.

*Skin ground color*.—Varies from a clear medium yellow to an orange yellow to a yellowish green (Yellow Group 2A-B, Yellow Group 13C, Yellow-Orange Group 14C and Yellow-Green Group 154A-C).

*Flesh color*.—Considered a medium to dark yellow (Yellow 13A-B and Yellow-Orange Group 14D) with red flecks appearing throughout (Red Group 46A).

*Flesh fibers*.—Present, numerous and lightly colored. These fibers are present throughout the flesh.

*Stone cavity flesh color*.—Medium yellow (Yellow Group 13A-B).

*Flesh texture*.—Generally, the flesh is considered firm and fine at commercial maturity.

*Ripening*.—Generally the fruit of the present variety ripens evenly.

*Flavor*.—Considered sweet and a rich, with slightly acidic flavor.

*Soluble solids*.—Range from 11 to 15 Brix with a mean of about 13 Brix.

*Titrable acidity*.—Generally ranges from 0.8-1.1 Eq $H^+$/1000 mL of juice depending on the ripeness of the fruit sampled.

*Aroma*.—Pleasant and reasonably abundant.

*Eating*.—Generally considered very good to excellent.

Stone:

*Attachment*.—Freestone at commercial maturity.

*Stone size*.—Generally considered medium-large relative to the ratio of stone to fruit size. Length — Approximately 31 to 34 mm. Width — Approximately 21 to 24 mm. Thickness — Approximately 16 to 18 mm.

*Fibers*.—Generally a few medium length fibers are attached sporadically along the surface of the stone. Stone Form — Elliptical. Stone Base — The stone is considered narrow. Apex Shape — Narrow. Stone Shape — The stone normally ovid.

*Stone surface*.—Surface Texture — Single pits and pit grooves. Ridges — Numerous fine ridges are present basally, and converge towards the base of the stone. Ventral Edge — None to small. Dorsal Edge — Shape — Grooved and having moderately rough edges. Stone Color — The color of the dry stone is light brown (165C-D of the Greyed-Orange Group). The color of the inside surface of the endocarp is primarily 159A-B of the Orange-White Group and 164D and 165D of the Greyed-Orange Group. Tendency to Split — Splitting was not observed. Kernel — The kernel fills the endocarp at harvest and measures approximately 4-5 mm in thickness, 9-10 mm in width, and 15-18 mm in length. When dried the shriveled kernels measure approximately 3 mm in thickness, 8-9 mm in width, and 16-17 mm in length. The colors of the shriveled kernels are primarily Greyed-Orange Group 165B-C. The kernels are viable if extracted from the endocarp and stratified immediately after harvest but not if allowed to dry first.

Use: The subject variety, 'ROYAL ZEST THREE', is considered to be a peach tree of mid-season maturity, which produces fruit which are very firm, attractively colored, and which are useful for both local and regional markets.

Keeping quality: Good.

Resistance to insects and disease: No particular susceptibilities were noted.

Shipping quality: Average.

Although the new variety of peach tree possesses the described characteristics when grown under the ecological conditions prevailing in the medium chill zone of Texas it will be understood that variations of the usual magnitude and characteristics incident to the changes in growing conditions, fertilization, pruning, and pest control are to be expected.

References

Anon. 2001. R.H.S. Colour Chart. The Royal Hort. Soc., London.

Brooks, R. M. 1958. Double Delight, Earligold, and June Gold peaches. Fruit Var. J. 3:22.

Brooks, R. M. and H. P. Olmo. 1997. Register of New Fruit and Nut Varieties. 3rd Edition. American Society of Horticultural Science Press, Alexandria, Va.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

Okie, W. R. 1993. 'Goldprince' and 'Scarletpearl' peaches. HortScience 28:231.

Okie, W. R. 1998. Handbook of peach and nectarine varieties, USDA, ARS, Agric. Handbook No. 714.

Rouse, R. and W. Sherman. 1989. 'TropicBeauty': a low-chilling peach for subtropical climates. HortScience 24:165-166.

Sherman, W. B. and P. M. Lyrene. 1992. Flordaprince peach. Fruit Var. J. 46:66-67.

Zaiger, C. F., G. N. Zaiger, L. M. Gardner, and G. G. Zaiger. 1990. Peach tree 'Rich Lady'. U.S. Plant Pat. No. 7,290. Aug. 7, 1990.

We claim:

1. A new and distinct *Prunus persica* tree, substantially as illustrated and described herein.

* * * * *